United States Patent
Doucet et al.

(10) Patent No.: US 8,388,693 B2
(45) Date of Patent: Mar. 5, 2013

(54) SURGICAL FASTENER FOR ATTACHING A HERNIA PROSTHESIS

(75) Inventors: Genevieve Doucet, Villefranche sur Saone (FR); Jean-Claude Sgro, Dijon (FR); Pierre Bailly, Caluire (FR)

(73) Assignee: Sofradim Production, Trevoux (FR)

( * ) Notice: Subject to any disclaimer, the term of this patent is extended or adjusted under 35 U.S.C. 154(b) by 712 days.

(21) Appl. No.: 12/421,140

(22) Filed: Apr. 9, 2009

(65) Prior Publication Data

US 2009/0259235 A1 Oct. 15, 2009

Related U.S. Application Data

(60) Provisional application No. 61/044,197, filed on Apr. 11, 2008.

(30) Foreign Application Priority Data

Nov. 4, 2008 (FR) ...................... 08 02004

(51) Int. Cl.
*A61F 2/02* (2006.01)
(52) U.S. Cl. .................................. 623/23.72
(58) Field of Classification Search .......... 606/75, 606/151, 213, 219, 205, 207, 210; 623/23.72
See application file for complete search history.

(56) References Cited

U.S. PATENT DOCUMENTS

| | | | | |
|---|---|---|---|---|
| 4,548,202 A * | 10/1985 | Duncan | ........................ | 606/220 |
| 5,258,000 A | 11/1993 | Gianturco | | |
| 5,425,740 A | 6/1995 | Hutchinson, Jr. | | |
| 5,509,922 A * | 4/1996 | Aranyi et al. | ................. | 606/205 |
| 5,634,931 A | 6/1997 | Kugel | | |
| 5,769,864 A | 6/1998 | Kugel | | |
| 5,810,851 A * | 9/1998 | Yoon | ............................. | 606/148 |
| 5,916,225 A | 6/1999 | Kugel | | |
| 6,171,318 B1 | 1/2001 | Kugel et al. | | |
| 6,174,320 B1 | 1/2001 | Kugel et al. | | |
| 6,176,863 B1 | 1/2001 | Kugel et al. | | |
| 6,224,616 B1 | 5/2001 | Kugel | | |
| 6,280,453 B1 | 8/2001 | Kugel et al. | | |
| 6,290,708 B1 | 9/2001 | Kugel et al. | | |
| 6,575,988 B2 * | 6/2003 | Rousseau | ...................... | 606/151 |
| 2003/0078602 A1 * | 4/2003 | Rousseau | ...................... | 606/151 |
| 2003/0130745 A1 | 7/2003 | Cherok et al. | | |
| 2004/0044364 A1 * | 3/2004 | DeVries et al. | ............... | 606/213 |
| 2004/0138705 A1 | 7/2004 | Heino et al. | | |
| 2005/0159777 A1 | 7/2005 | Spitz | | |
| 2005/0267478 A1 * | 12/2005 | Corradi et al. | ................. | 606/73 |
| 2006/0282105 A1 | 12/2006 | Ford et al. | | |

FOREIGN PATENT DOCUMENTS

| | | |
|---|---|---|
| EP | 0 557 964 | 9/1993 |
| FR | 2 719 993 | 11/1995 |

(Continued)

*Primary Examiner* — Melanie Tyson
*Assistant Examiner* — Son Dang
(74) *Attorney, Agent, or Firm* — Carter, DeLuca, Farrell & Schmidt, LLP

(57) ABSTRACT

The present disclosure relates to a surgical fastener for attaching a prosthesis intended to repair a hernial defect of the abdominal wall, the prosthesis has at least two layers made of a biocompatible flexible material joined together at least one assembly zone, so as to define an internal space delimited by a substantially circular peripheral contour. The internal space is accessible to said surgical fastener that includes at least one body forming a reinforcing section that includes an open ring intended to extend substantially along at least one part of the substantially circular substantially circular peripheral contour. The open ring is connected to an attachment arm that extends substantially radially towards the inside and is intended to be anchored in the abdominal wall.

14 Claims, 5 Drawing Sheets

FOREIGN PATENT DOCUMENTS

| | | |
|---|---|---|
| GB | 1 406 271 | 9/1975 |
| WO | WO 96/09795 | 4/1996 |
| WO | WO 99/06080 | 2/1999 |
| WO | WO 00/07520 | 2/2000 |
| WO | WO 01/89392 | 11/2001 |
| WO | WO 2004/012627 | 2/2004 |

* cited by examiner

SURGICAL FASTENER FOR ATTACHING A HERNIA PROSTHESIS

RELATED APPLICATIONS

This application claims priority to provisional application Ser. No. 61/044,197, filed Apr. 11, 2008 and French application FR 08/02004 filed Apr. 11, 2008.

TECHNICAL FIELD

The present disclosure relates to a surgical fastener that allows the fitting of a prosthesis intended, in particular, for plugging hernias, and also a kit including this surgical fastener and a prosthesis.

BACKGROUND

The abdominal wall in humans is made up of fat and muscles joined together by aponeuroses. Sometimes a hiatus occurs at the aponeuroses that allows part of the peritoneum to protrude which then constitutes a sac, or else a hernia, containing either fat or part of the intestines. Hernias or eventrations (hernia occurring over a surgical parietal scar) appear as an excrescence at the surface of the skin and are qualified as hernias or eventrations, for example umbilical or inguinal depending on their locations.

The most conventional method for repairing a hernial defect involves attaching suture threads under tension. However, this type of repair is a source of pain for the patient and, due to the high tensions, have a not insignificant risk of tearing muscles and aponeuroses via the sutures and/or of recurrence of the hernia.

In order to minimize the risks of recurrence, surgeons frequently insert a prosthesis made of a synthetic mesh which replaces or reinforces the weakened anatomical tissues without requiring the edges of the damaged tissues to be brought together. However, such a prosthesis is subjected to an abdominal pressure which tends to expel it outwards. Hence the effectiveness of the prosthesis, and therefore the minimization of the risks of relapse, depend in large part on the attachment of this prosthesis. Firstly, the spreading-out of the prostheses, which are often flexible, proves difficult so that they have a tendency to form folds over the abdominal wall. The lack of perfect spreading-out leads to a risk of herniation of the peritoneal sac and increases the possibilities of recurrence. The surgeon therefore tries to ensure that no part of the prosthesis is folded over and that no viscera or no part of the intestines is interposed between the prosthesis and the abdominal wall. Then, poor positioning of the sutures or poor attachment of the prosthesis risks twisting this prosthesis and creating tensions.

In order to attempt to overcome these drawbacks, various types of prosthesis have been proposed.

Published patent application US 2005/0159777 discloses a device intended to facilitate the spreading-out of the prosthesis in the peritoneal space using an inflatable balloon. However, the correct positioning of the prosthesis is difficult to maintain between the removal of the balloon and the introduction of the stapling device. Furthermore, the use of this device requires a prior incision in the peritoneal sac at the risk of tearing it. Finally, the positioning of the staples is carried out without direct visual control, by means of a complex stapler, which does not make it possible to ensure that no small intestine loop or that no fat fold is interposed between the prosthesis and the posterior face of the abdomen.

Published international patent application WO-A-00/07520 discloses a flexible mesh prosthesis that is kept taut by a ring having a flexibility, which enables it to be deformed then to resume its initial shape. However, it is observed that the introduction of this type of prosthesis is made difficult due to the presence of the ring. Furthermore, these flat and rigid prostheses do not always fit correctly to the convexity of the peritoneal sac and viscera. Moreover, this type of prosthesis does not make it possible to ensure correct attachment and centring.

One variant disclosed in published patent application US 2006/0282105 consists of a prosthesis containing a resilient rod capable of keeping the prosthesis in the deployed position. The attachment of the prosthesis is obtained by a resorbable tether passed through the abdominal wall. Keeping the prosthesis in position is then only ensured by the abdominal pressure and a risk of herniation of the peritoneal sac is therefore not ruled out.

SUMMARY

The present surgical fastener facilitates the spreading-out and the attachment of a prosthesis that can be used for the surgical treatment of hernias, in particular, but not only, for the surgical treatment of small-size hernias. The surgical fastener also provides the rigidification of a flexible prosthesis.

Surgical kits for the treatment of a hernial defect of the abdominal wall are also described.

In the present application, the term "prosthesis" is understood to mean a biocompatible medical device that can be implanted in the human or animal body.

According to the present disclosure, a surgical fastener is provided for attaching a prosthesis intended to repair a hernial defect of the abdominal wall. The prosthesis includes at least a first layer made of a biocompatible flexible material intended to be placed facing the abdominal wall and at least a second layer made of a biocompatible flexible material intended to be placed facing the abdominal cavity. The first and second layers of the prosthesis are joined together at least one assembly zone, so as to define an internal space delimited by a substantially circular peripheral contour. The internal space is accessible to the present surgical fastener by means of an introduction opening made in at least one of the first or second layers. The surgical fastener includes at least one body that forms a reinforcing section having an open ring that may be substantially planar and intended to extend substantially along at least one part of the substantially circular peripheral contour. The open ring defines two opposite ends. The fastener can be introduced via the introduction opening into the internal space via at least one of the ends, one of the ends of the open ring being connected to an attachment arm that extends substantially radially towards the inside of the open ring and is intended to be anchored in the abdominal wall.

The fastener according to the present disclosure, due to its sectional shape that has two opposite ends, one of which may be introduced into the internal space of the prosthesis, makes it possible to rigidify the prosthesis after it has been introduced over the implantation site. Thus, owing to the rigidifying fastener of the present disclosure, it is possible to use a particularly flexible prosthesis, which may therefore be introduced into the body of the patient via a minimal incision. Thus, the present surgical fastener is particularly useful in the case of umbilical hernias, for which the defect to be repaired is small and for which prostheses of small dimensions are recommended. The trauma for the patient is minimized.

In embodiments, the open ring forms an angular sector of at least 270°, in embodiments an angular sector of at least 340°, in other embodiments an angular sector of at least 350°.

In embodiments, the reinforcing section is made from a substantially rigid material. As used herein, the term "rigid" is understood to mean that the reinforcing section cannot be deformed in order to be introduced into the hernial defect. This is because, generally, the size of the reinforcing section, due to the fact that this reinforcing section is intended to extend substantially along at least one part of the substantially circular peripheral contour of the prosthesis, will be greater than the hernial defect. According to such embodiments, the reinforcing section has a rigidity such that it cannot be reduced during the introduction of the surgical fastener into the hernial defect. It is the geometry of the open ring, which allows it to be introduced. Thus, once the open ring is introduced into the prosthesis as explained below, the prosthesis cannot be deformed and remains rigidified even in the case of pressures exerted on it and/or on the open ring.

In embodiments, the surgical fastener includes a substantially flat reinforcing section. Thus, the prosthesis attached by the surgical fastener has a surface that is substantially flat and is not very traumatic for the viscera.

In embodiments, the connection between the attachment arm and the open ring enables the attachment arm to extend in several different planes.

In embodiments, the attachment arm is equipped with attachment means. Advantageously, the attachment means may include concentric outer grooves or outer ribs that form a harpoon.

In embodiments, an orifice may be made in the attachment arm in order to enable the attachment of the attachment arm into the abdominal wall using a suture thread.

In embodiments, the attachment arm consists of a single piece with the reinforcing section.

In embodiments, the connection between the attachment arm and the open ring is a bend of the reinforcing section.

In embodiments, the various components of the surgical fastener may be composed of different materials.

In embodiments, the two ends of the open ring are facing one another. Advantageously, the ends may be able to be attached to one another.

In embodiments, the surface of the surgical fastener is substantially smooth. Such a surface makes it possible to facilitate the insertion of the surgical fastener into the internal space via the introduction opening of the prosthesis.

The attachment arm may have dimensions independent of those of the prosthesis. In particular, the attachment arm may have a length greater than the largest of the dimensions of the prosthesis.

In embodiments, the surgical fastener is made from a non-resorbable material.

In other embodiments, the surgical fastener is made from a bioresorbable material.

In the present application, the term "bioresorbable" is understood to mean the characteristic according to which a material is absorbed by the biological tissues and disappears in vivo at the end of a given period, which may vary, for example, from one day to several months, depending on the chemical nature of the material.

The bioresorbable material suitable for the surgical fastener according to the present disclosure may be chosen from polylactic acid (PLA), polycaprolactones (PCLs), polydioxanones (PDOs), trimethylene carbonates (TMCs), polyvinyl alcohol (PVA), polyhydroxyalkanoates (PHAs), oxidized cellulose, polyglycolic acid (PGA), copolymers of these materials and mixtures thereof.

In embodiments, the bioresorbable material suitable for the surgical fastener according to the disclosure may be chosen from polylactic acid (PLA), polyglycolic acid (PGA), copolymers of these materials and mixtures thereof.

A surgical fastener according to the present disclosure made from bioresorbable material makes it possible to ensure the rigidification of a prosthesis for the time necessary for the colonization of the prosthesis. Thus, when a flexible prosthesis is used, this has the advantage of being more comfortable and better tolerated by the patient, particularly when the surgical fastener has been resorbed.

A surgical kit for treating a hernial defect of the abdominal wall in accordance with the present disclosure includes:
  a. a surgical fastener according to the present disclosure; and
  b. a prosthesis intended to repair the hernial defect, the prosthesis including at least a first layer made of a biocompatible flexible material intended to be placed facing the abdominal wall and at least a second layer made of a biocompatible flexible material intended to be placed facing the abdominal cavity, the first and second layers being joined together at least one assembly zone, so as to define an internal space delimited by a substantially circular peripheral contour, the internal space being open via at least one orifice made in the first layer and/or an introduction opening made in at least one of the first or second layers.

In embodiments, the prosthesis contained in the surgical kit includes at least one return thread intended to be attached in the vicinity of the introduction opening. Such a thread enables the surgeon to easily position the introduction opening opposite the incision made in the skin of the patient, once the prosthesis is introduced into the implantation site.

In embodiments, one or both of the layers of the prosthesis of the surgical kit is made up of an arrangement of yarns.

In the present application, the arrangement of yarns or of portions of yarns may result from weaving or else knitting. A knit suitable for the prosthesis of the kit according to the present disclosure may be what is referred to by those skilled in the art as a three-dimensional knit, for example as described in published international patent application WO 99/06080. The expression "three-dimensional knit" is understood in the sense of the present application to mean an assembly or arrangement of monofilament or multifilament yarns, obtained by knitting and having two opposite faces separated from one another by a significant thickness, for example at least 0.5 mm.

Such a knit maybe knitted, for example, on a chain or Raschel loom using four or six guide bars, four guide bars producing two layers of yarns, each layer of yarns forming one face of the fabric, and the two other guide bars producing a connector or linking layer of yarns connecting the two opposite faces of the knit. In the present application, the term "connector" is understood to mean the layer or layers of yarns that connect the two faces of a three-dimensional knit to one another, thus constituting the thickness of such a knit.

In embodiments, the prosthesis of the surgical kit may include one or more two-dimensional knits. The expression "two-dimensional knit" is understood in the sense of the present application to mean a knit having two opposite faces, free from a linking layer of yarns between these two faces.

In embodiments, the first layer of the prosthesis may include a two-dimensional knit and the second layer a three-dimensional knit.

In embodiments, the first and second layers of the prosthesis include a two-dimensional knit and are assembled, at the edges of the prosthesis, by a three-dimensional knit.

In other embodiments, the first and second layers of the prosthesis are assembled, at the edges of the prosthesis, by internal stitching. Thus, the edges of the prosthesis are atraumatic.

When the yarns or portions of yarns are used to constitute the prosthesis of the surgical kit according to the present disclosure, these yarns may be chosen from yarns or portions of yarns that are resorbable and/or non-resorbable or a mixture thereof.

Thus, mention may be made, as bioresorbable materials suitable for the yarns and/or portions of yarns according to the present disclosure, of polylactic acid (PLA), polycaprolactones (PCLs), polydioxanones (PDOs), trimethylene carbonates (TMCs), polyvinyl alcohol (PVA), polyhydroxylkanoates (PHAs), oxidized cellulose, polyglycolic acid (PGA), copolymers of these materials and mixtures thereof.

Mention may be made, as suitable non-bioresorbable materials of polypropylenes, polyesters such as polyethylene terephthalates, polyamides and mixtures thereof.

The yarns and/or portions of yarns may, for example, be chosen from monofilament yarns, multifilament yarns and a combination thereof.

In embodiments of the surgical kit, the prosthesis is impregnated with purified collagen. The use of purified collagen makes it possible to thus promote the colonization of the prosthesis by the scar tissues.

In embodiments, the second layer of the prosthesis of the kit is covered with an anti-adhesion coating on its face intended to be positioned facing the abdominal cavity.

The term "anti-adhesion" is understood in the sense of the present application to mean a smooth and non-porous biocompatible coating or material that does not offer space for cellular recolonization.

The anti-adhesion material or coating is chosen from bioresorbable materials, non-bioresorbable materials and mixtures thereof. Non-bioresorbable anti-adhesion materials may be chosen from polytetrafluoroethylene, polyethylene glycols, polysiloxanes, polyurethanes, stainless steels, derivatives of precious metals and mixtures thereof.

In embodiments, the anti-adhesion material or coating is bioresorbable. Bioresorbable materials suitable for the anti-adhesion coating may be chosen from collagens, oxidized celluloses, polyacrylates, trimethylene carbonates, caprolactones, dioxanones, glycolic acid, lactic acid, glycolides, lactides, polysaccharides, for example chitosans, polyglucuronic acids, hyaluronic acids, dextrans and mixtures thereof.

In embodiments, the material forming the anti-adhesion coating is a hydrophilic bioresorbable material, such as, for example, collagens, polysaccharides and mixtures thereof.

Among the collagens that can be used according to the present disclosure mention may be made of:
  collagen, the helical structure of which is at least partially thermally denatured, without hydrolytic degradation, the preparation method for which is described in WO 99/06080;
  filmed, unheated, native collagen with or without glycerol, crosslinked by gamma irradiation or by other chemical or physical means,
  and/or mixtures thereof.

Among the polysaccharides that can be used as resorbable hydrophilic material mention may be made of oxidized cellulose, hyaluronic acid, starch, chitosan, crosslinked dextrans and/or mixtures thereof. All these materials are well known to a person skilled in the art. As an oxidized cellulose that is suitable for use on the present prosthesis, mention may be made of the product sold under the trade name INTERCEED® by Ethicon Inc., Somerville, N.J., USA. As a hyaluronic acid that is suitable for use on the present prosthesis, mention may be made of the product sold under the trade name HYALOBARRIER® by Fidia Advanced Biopolymers, Abano Terme, Italy, or the product sold under the trade name SEPRAFILM® by Genzyme, Cambridge, Mass., USA.

The anti-adhesion coating according to the present disclosure makes it possible to protect, at least during the initial healing phase, the second layer of the prosthesis, namely that which is not exposed to the inflammatory cells, such as granulocytes, monocytes, macrophages or else multinucleated giant cells generally activated by the surgical procedure. This is because, at least during the initial healing phase, the duration of which may vary from 5 to 10 days approximately, only the anti-adhesion coating is accessible to the various factors such as proteins, enzymes, cytokines or the inflammatory cells, at the first textile part.

In the case where the anti-adhesion coating is made up of non-resorbable materials, it thus protects the coated prosthesis layer before and after implantation, throughout the implantation life of the prosthesis.

Furthermore, owing to the anti-adhesion coating, the surrounding delicate tissues such as, for example, the hollow viscera are protected, in particular from the formation of undesired severe post-surgical fibrous adhesions.

In the case where the anti-adhesion material includes a bioresorbable material, the bioresorbable material may be chosen such that it does not resorb before several days so that the anti-adhesion coating can carry out its role of protecting the intestine and hollow organs during the days following the operation, and until the cellular rehabilitation of the prosthesis in turn protects the delicate organs.

According to certain embodiments, the prosthesis of the surgical kit includes at least one layer that is non-bioresorbable. Thus, the reinforcing function of the prosthesis is permanent.

In order to facilitate the introduction of the prosthesis into the abdominal cavity while avoiding contamination of the inner layers of the anatomical tissues with pathogenic microorganisms, the surgical kit according to the present disclosure may additionally include a system for introducing the prosthesis into the abdominal cavity.

The surgical kit may additionally include a surgical instrument for positioning the prosthesis, the surgical instrument having at least one proximal gripping zone and at least one distal body, the distal body being equipped with clamping means capable of grasping the first layer in the vicinity of the introduction opening and of moving it away from the second layer.

BRIEF DESCRIPTION OF THE DRAWINGS

Other features and advantages will appear throughout the description which follows of one particular embodiment, given solely by way of non-limiting example, with regard to the drawings which represent.

DETAILED DESCRIPTION OF PREFERRED EMBODIMENTS

Figure 1:
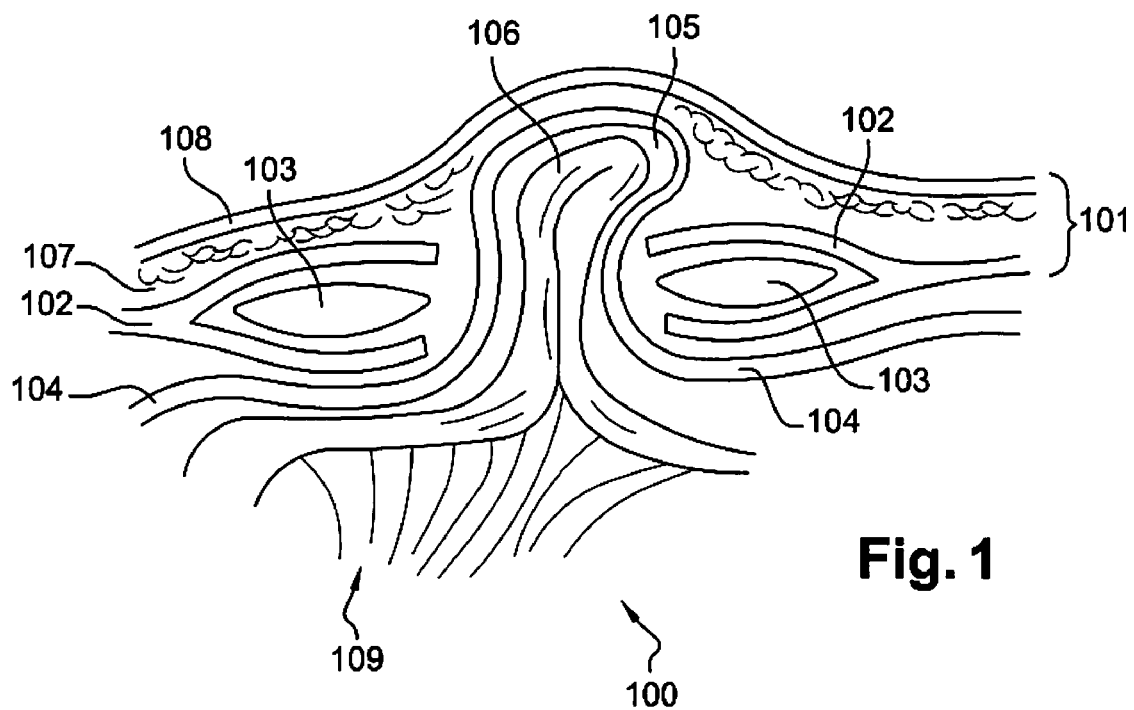
FIG. 1 is a cross-sectional representation of a median abdominal hernia or eventration.

FIG. 1 represents a hernial defect 100 of the abdominal wall 101 which is characterized by a hiatus of the aponeurosis 102 surrounding the rectus muscles 103 and a passage of the peritoneum 104 forming a sac, the hernial sac 105, which contains either fat (omentum) or some of the viscera 106, and which then puts pressure on the fatty tissues 107 and is flush with the skin 108. One treatment for a hernial defect 100 consists in replacing and holding the viscera 106 in the abdominal cavity 109.

Figure 2:
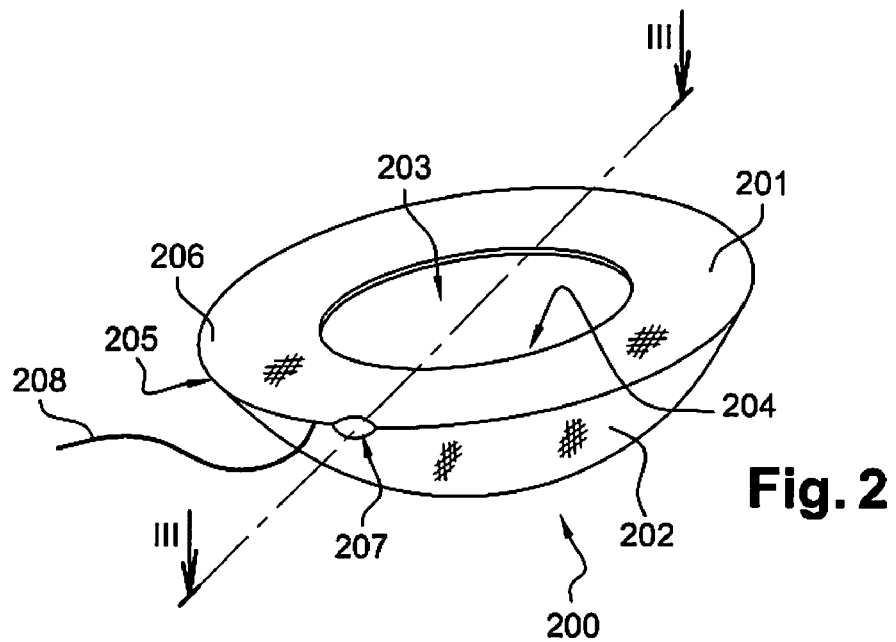
FIG. 2 is a perspective representation of a prosthesis contained in the kit according to the present disclosure.

FIG. 2 represents a prosthesis 200 capable of repairing a hernial defect 100 of the abdominal wall 101, prosthesis 200 including at least a first layer 201 made of a biocompatible flexible material intended to be placed facing the abdominal wall 101 and at least a second layer 202 made of a biocompatible material intended to be placed facing the abdominal cavity 109. The first and second layers (201, 202) are joined together so as to define an internal space 203 that is open via an orifice 204 made in first layer 201 and that extends to a zone 205 for assembling the first and second layers (201, 202). The internal space is delimited by the substantially circular peripheral contour 206, represented in FIG. 2 in a circular form, of the assembly zone 205. An introduction opening 207 is made in at least one of the first and/or second layers (201, 202). The introduction opening 207 is advantageously positioned in the vicinity of or on the substantially circular peripheral contour 206. However, the introduction opening 207 may, in one embodiment that is not shown, be merged with the orifice 204 made in first layer 201. At least one return thread 208 may advantageously be positioned in the vicinity of introduction opening 207. Such a thread allows the surgeon to easily position the introduction opening 207 opposite the incision made in the skin of the patient, once the prosthesis is introduced into the implantation site.

Figure 3:
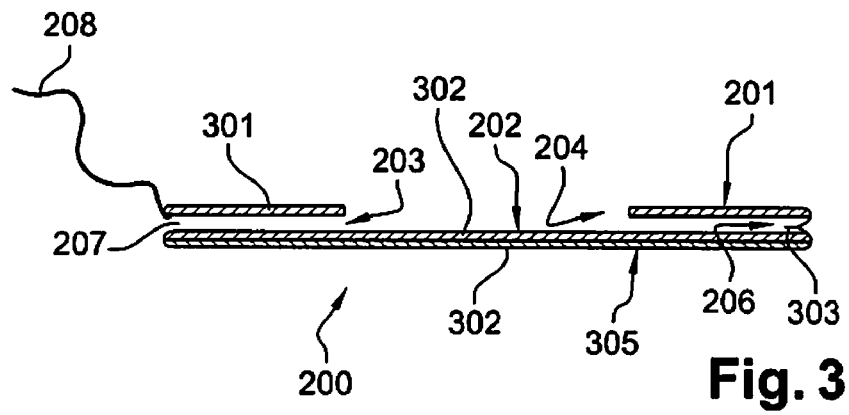
FIG. 3 is a transverse cross-sectional representation along the axis III-III of the prosthesis from FIG. 2.

The transversal cross-sectional view from FIG. 3 shows the composition of the prosthesis 200 represented in FIG. 2. In particular, it can be seen how the first layer 201 formed from a two-dimensional arrangement of yarns 301 and the second layer 202, made up of a two-dimensional arrangement of yarns 302, are joined at their periphery by internal stitching 303, that makes it possible to obtain a prosthesis 200 for which the edges are atraumatic. This internal stitching 303 defines the substantially circular peripheral contour 206 of the internal space 203 of the prosthesis 200. In another embodiment that is not shown, the first and second layers (201, 202) are joined together by a three-dimensional knit. The yarns constituting the arrangements of yarns (301, 302) may be chosen from resorbable and/or non-resorbable yarns. An anti-adhesion coating 305, which may advantageously be bioresorbable, can cover the arrangement of yarns 302 of the second layer 202 in order to avoid, in particular, the formation of undesired severe post-surgical fibrous adhesions.

Figure 4:
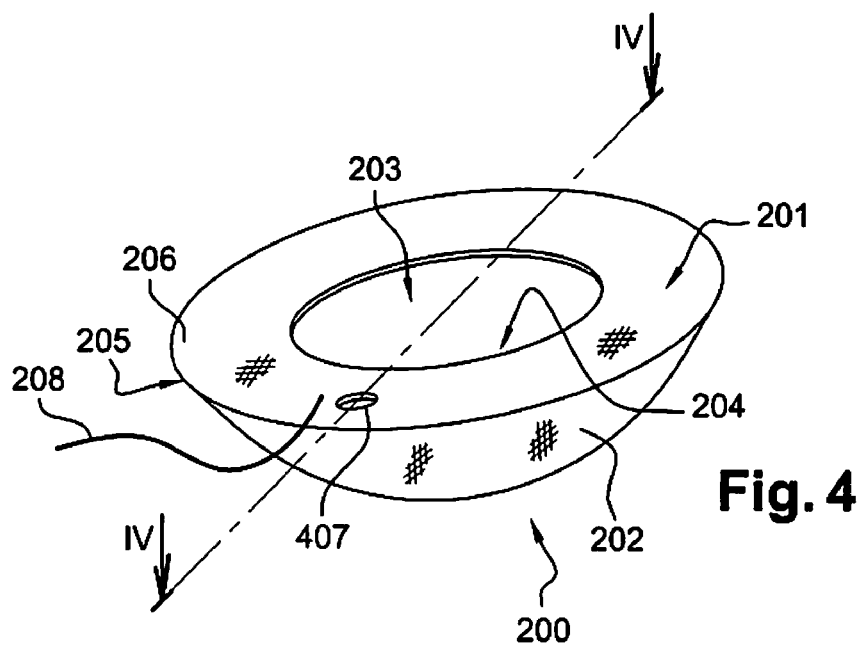
FIG. 4 is a perspective representation of another embodiment of a prosthesis contained in the kit according to the present disclosure.
Figure 5:
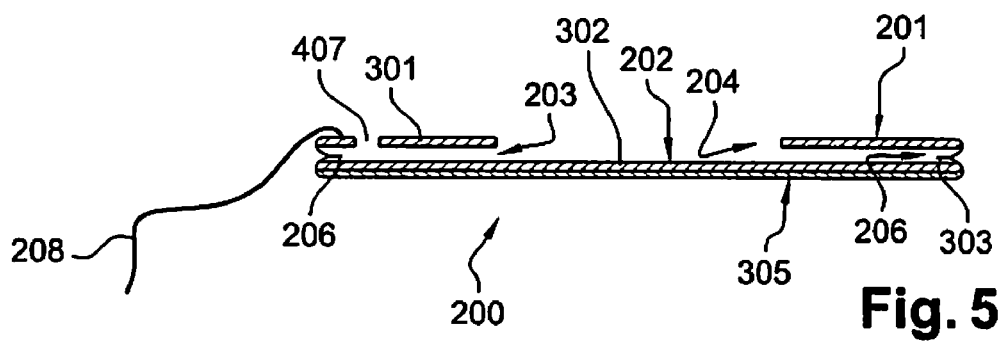
FIG. 5 is a transverse cross-sectional representation along the axis IV-IV of the prosthesis from FIG. 4.

FIGS. 4 and 5 show another embodiment of the prosthesis according to the present disclosure in which the introduction opening 407 is made in the first layer 201 only.

Figure 6:
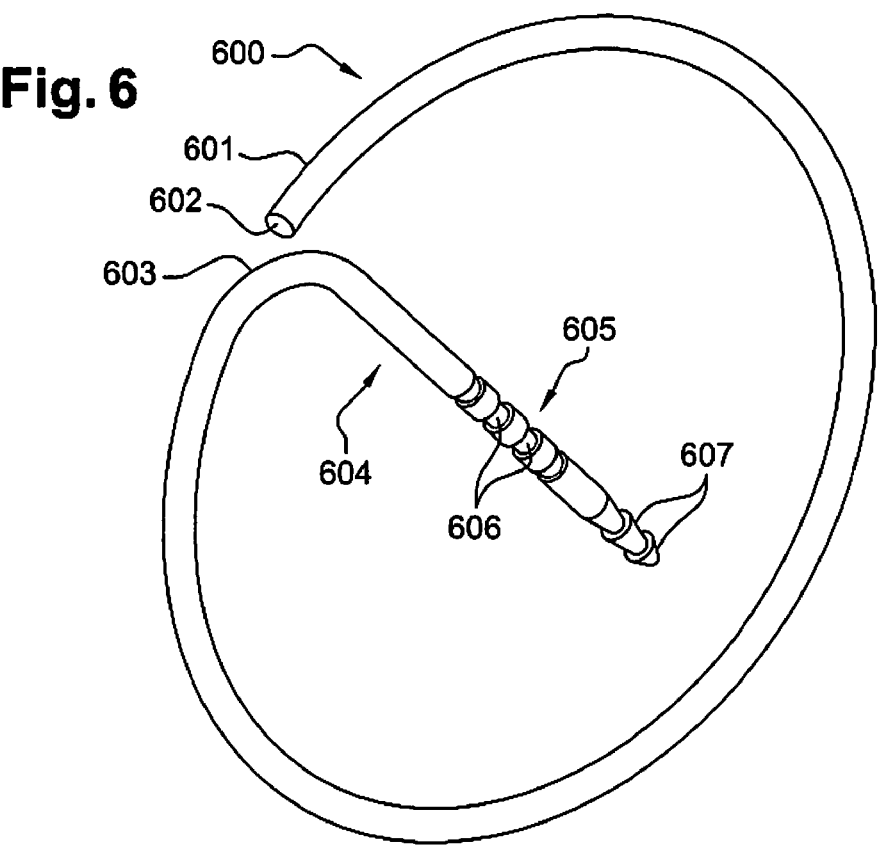
FIG. 6 is a perspective representation of a surgical fastener according to the present disclosure.
Figure 10:
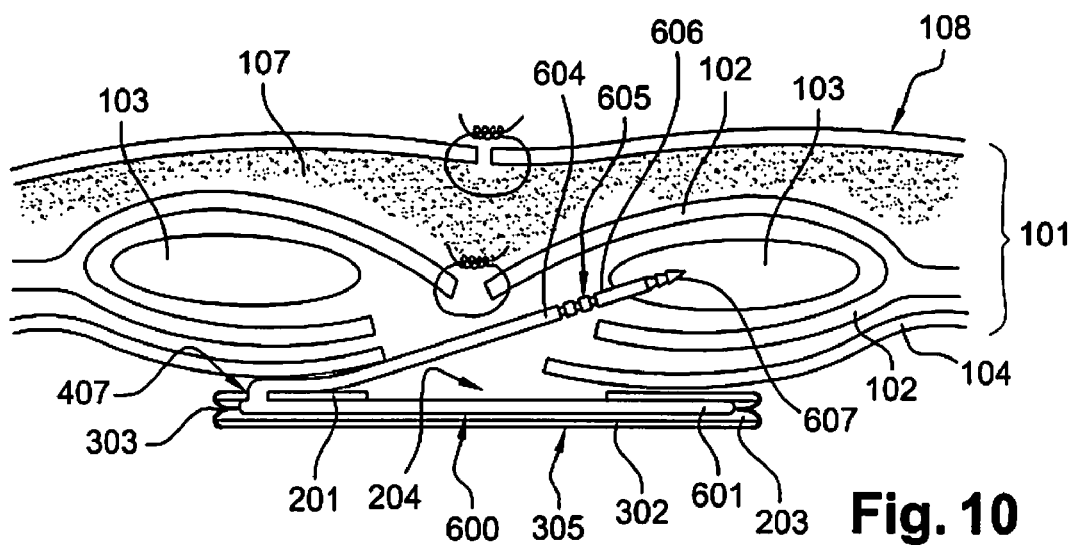
FIG. 10 is a cross-sectional representation of a repair of a hernial defect which has been carried out using a prosthesis contained in the kit according to the present disclosure and attached by at least one surgical fastener according to FIG. 6.

FIG. 6 represents a surgical fastener 600 according to the present disclosure, made up of a reinforcing section including an open ring 601 substantially included into one plane. In the example shown, the open ring 601 has two opposite ends (602, 603), one free end 602 and one end 603 which is connected to an attachment arm 604 that extends substantially radially towards the inside of open ring 601. In the example shown, the two ends (602, 603) of the section 601 are facing one another. Attachment arm 604 is equipped with attachment means 605 including concentric outer grooves 606 and outer ribs that form a harpoon 607 intended to anchor the fastener in the abdominal wall 101 (cf. FIG. 10). In this embodiment, the attachment arm 604 is specifically intended to pass through at least one part of the abdominal wall 101, as is shown in FIG. 10, that is to say optionally through the peritoneum 104 and at least through the aponeuroses 102 and/or the rectus muscles 103. The attachment means 605 arranged on attachment arm 604 make it possible to ensure an attachment of the surgical fastener 600 into the abdominal wall 101 as is shown in FIG. 10.

The surgical fastener 600 shown on FIG. 6 can be, for example, made of a rod forming an open ring (601) and a bend wherein one end of the rod extends radially towards the inside to constitute attachment arm (604). Thus, the open ring (601) allows the surgical fastener 600 to be easily introduced into the internal space 203 via the end 602.

In embodiments, the reinforcing section is rigid. Thus, once the section is introduced into the internal space 203 of the prosthesis 200, it can no longer be deformed, ensuring better security. Such rigidity of the reinforcing section therefore allows the use of a flexible prosthesis 200 that is more easily introduced into the hernial defect 100. In embodiments, the open ring forms an angular sector of at least 270°, in other embodiments at least 350°, so that it can extends along most of the substantially circular peripheral contour 206 to help expanding the prosthesis 200 and to provide a good rigidity to the prosthesis 200. The reinforcing section includes an open ring, which is open in order to be introduced into the internal space 203. However, the sector on which the ring is open is may be as small as possible. This fastener may be made from a bioresorbable material, for example from PLA, PGA or a mixture of these polymers.

In one example which is not shown, the two ends of the section can be attached to one another once the fastener has been introduced into the prosthesis, for example by means of a male connector located on one of the ends and a complementary female connector located on the other end. After introducing the fastener inside the internal space 203 of prosthesis 200, as explained, for example, in FIG. 7 below, the two ends may be connected to close up the circle formed by the section. The prosthesis is thus perfectly rigidified.

Figure 7:
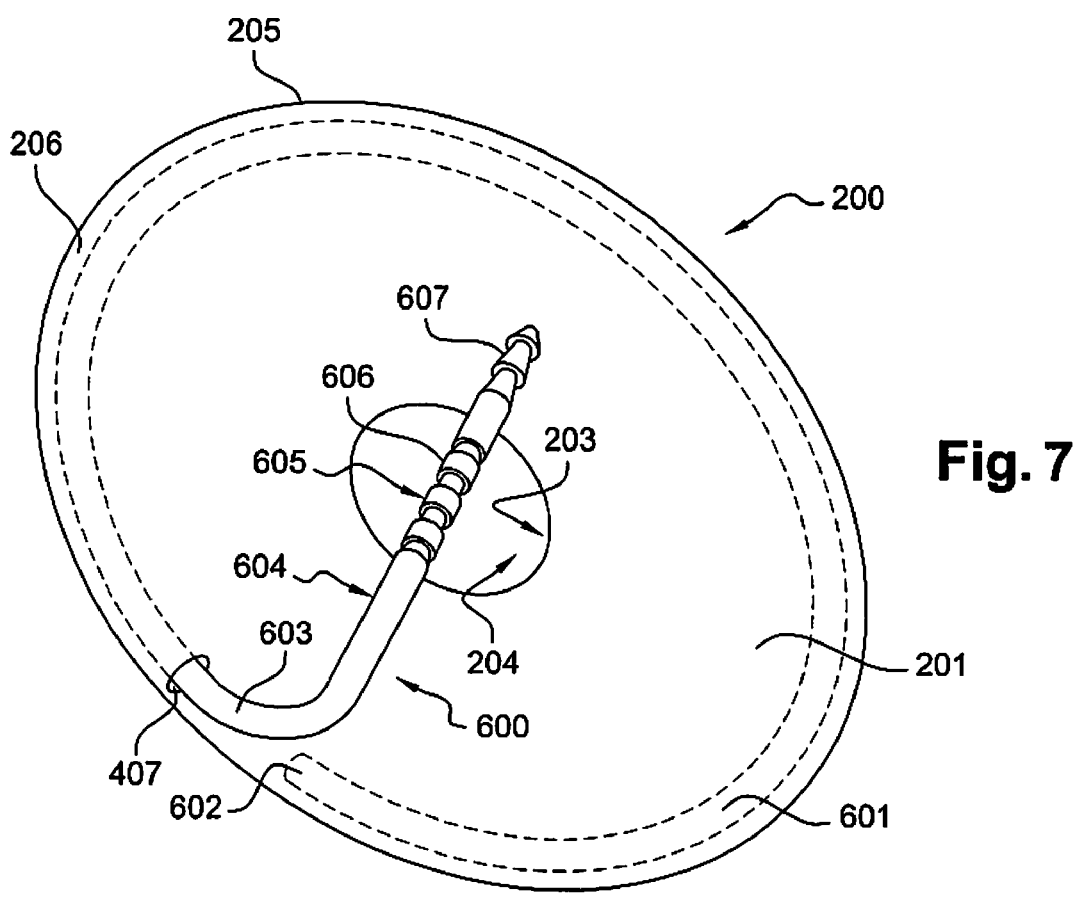
FIG. 7 is a perspective representation of a surgical fastener according to the present disclosure introduced into the internal space of a prosthesis contained in a kit according to the present disclosure.

FIG. 7 represents the surgical fastener from FIG. 6 introduced into a prosthesis as represented in FIG. 4. The free end 602 of the fastener 600 has been introduced into the introduction opening 407. By transmitting a rotational movement to the attachment arm 604, the free end 602 progresses substantially along the substantially circular peripheral contour 206 of prosthesis 200 until the end 603 is brought into the vicinity of the introduction opening 407. Advantageously, a substantially smooth surface of the surgical fastener 600 makes it possible to facilitate the progression of fastener 600 along the substantially circular peripheral contour 206 while minimizing potential friction between the open ring 601 and the knit or knits forming the prosthesis 200. In order to further facilitate the introduction of the fastener 600 into the internal space 203 of the prosthesis 200, while avoiding the rotation of the prosthesis 200 concomitantly to the rotation of the surgical fastener 600, the return thread 208 makes it possible to attach, temporarily or otherwise, the prosthesis to the abdominal wall 101 (cf. FIG. 10). The surgical fastener 600 is then suitably positioned in the prosthesis 200, the open ring 601 extending substantially along the substantially circular peripheral contour 206 and the attachment arm 604 extending outwards from prosthesis 200. The open ring 601 makes it possible, in this position, to rigidify and maintain the correct deployment of the prosthesis 200 while avoiding the formation of folds in the second layer 202. Advantageously, the open ring 601 is substantially flat, that is, included into one plane, in order to prevent the formation of such folds.

Figure 11:
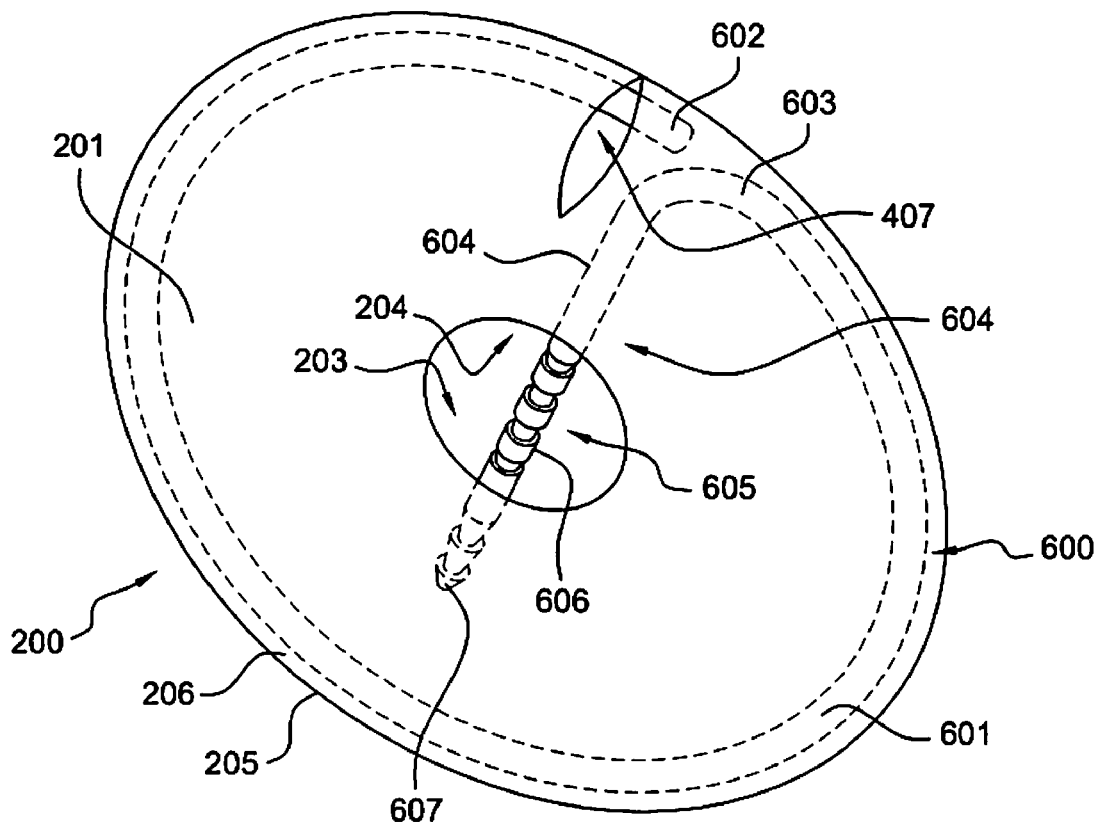
FIG. 11 is a perspective representation of a surgical fastener from FIG. 6 introduced entirely into the internal space of a prosthesis contained in the kit according to the present disclosure.

In the case where the introduction opening (407, 207) and the orifice 204 are merged, the common opening may have, in particular, the shape of a slot allowing introduction of the surgical fastener 600 from FIG. 6. This introduction may be, in this case, carried out either by the free end 602 of the surgical fastener 600 or by the attachment arm 604. When the attachment arm 604 is first introduced into the internal space 203, the attachment arm may or may not then be kept entirely in the internal space 203 of the prosthesis 200, as shown in FIG. 11.

In order to repair a hernial defect 100 using a prosthesis 200 from FIG. 2 or 4 according to the present disclosure, the surgeon makes an arc-shaped incision along one half of the lower or lateral circumference of hernial defect 100 (cf. FIG. 1) then dissects the hernial sac 105 which generally adheres to the lower part of the cutaneous teguments. The surgeon may be aided, for this dissection, by introducing a finger into the depression of the umbilicus. The hernial sac 105 is then completely released and unsecured in order to suppress the adhesions.

A prosthesis contained in the kit according to the present disclosure, such as those represented in FIG. 2 or 4 for example, is introduced into the hernial defect 100. Such a prosthesis 200 does not have a rigidifying component: it is very flexible and may be introduced into the hernial defect 100 very easily by folding it.

One part of at least one return thread 208, previously attached to prosthesis 200, is kept outside of hernial defect 100. The at least one return thread 208 will be used to bring the introduction opening 207, 407 into the vicinity of the hernial orifice via a slight tension on return thread 208.

Figure 8:
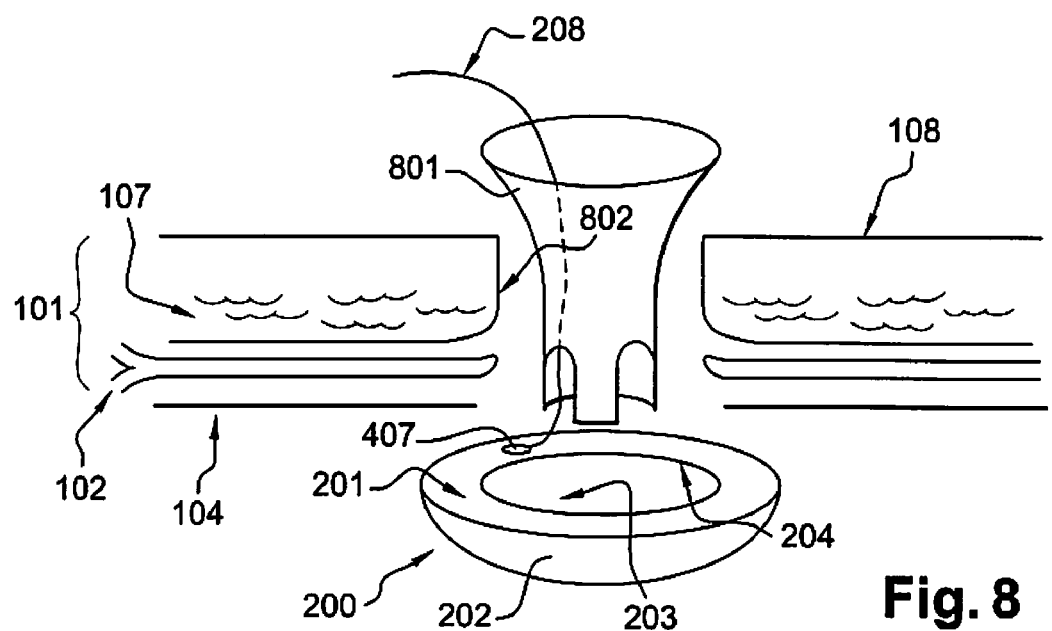
FIG. 8 is a schematic representation of an introduction system and of a prosthesis contained in a kit according to the present disclosure.

Advantageously, as shown in FIG. 8, an introduction system 801 may be used to enable the introduction of a prosthesis 200 while preventing it from coming into contact with the outer layers of the abdominal wall 802. The surgical kit according to the present disclosure may therefore include, besides at least one surgical fastener 600 from FIG. 6, a prosthesis 200 and at least one return thread 208, and an introduction system 801. Such an introduction system 801 may be formed from a material such as polyethylene, polyurethane, polypropylene or stainless steel.

The surgeon then introduces the surgical fastener 600 from FIG. 6 into the introduction opening (207, 407) in order to position fastener 600 in the prosthesis as shown in FIG. 7. The use of a flexible prosthesis 200, the shape of the surgical fastener 600 and its method of introduction into the internal space 203, which consists in introducing the free end 602 of the open ring 601 into the introduction opening (207, 407) previously brought opposite the incision using the return thread or threads 208 then in making section 601 slide along the substantially circular peripheral contour, has the advantage of enabling the positioning of a prosthesis 200 and of a surgical fastener 600 in the abdominal cavity 109 of a patient, via a minimum incision. The prosthesis and the appropriate fastener may have dimensions greater than the incision made in order to introduce them. In embodiments, the open ring 601 is rigid.

Figure 9:
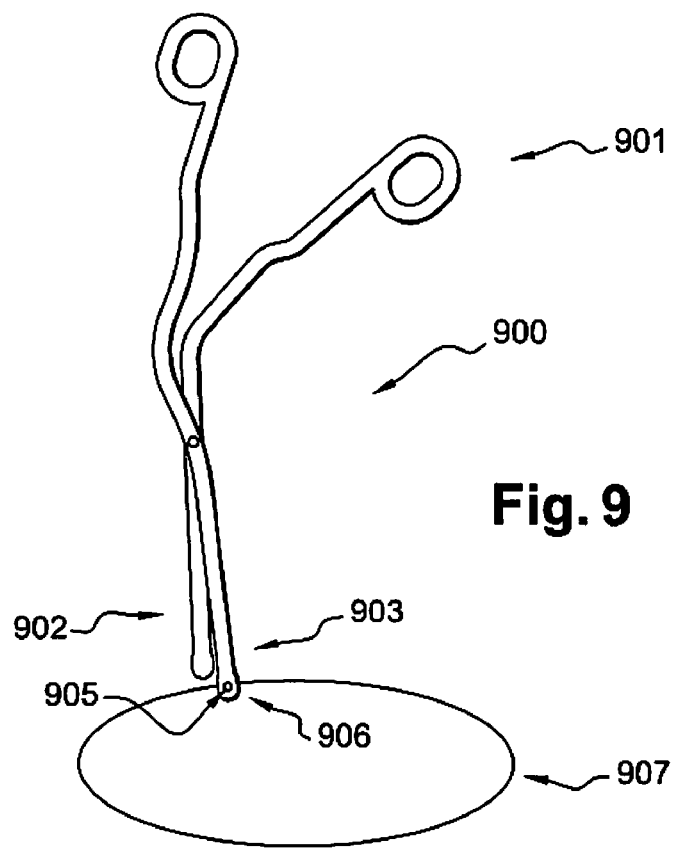
FIG. 9 is a perspective representation of a surgical instrument according to the present disclosure, capable of grasping the first layer of a prosthesis and of keeping it apart from the second layer of the prosthesis contained in the kit according to the present disclosure.

The initial deployment of prosthesis 200, before it is introduced into the abdominal cavity 109, may be carried out using a surgical instrument 900 shown in FIG. 9 in order to facilitate the progression of the surgical fastener 600 along the substantially circular peripheral contour 206 of prosthesis 200. Such an instrument is particularly useful when the prosthesis used is flexible. Once the surgical fastener is introduced into the internal space 203 of the prosthesis 200, surgical instrument 900 may be removed.

FIG. 9 represents a surgical instrument 900 for positioning prosthesis 200. Surgical instrument 900 includes at least one proximal gripping zone 901 and at least one distal body 902. Distal body 902 is equipped with clamping means 903 capable of grasping the first layer 201 in the vicinity of introduction opening (207, 407) and of moving it away from second layer 202. In the example shown, the clamping means is made up of the jaws of a pair of surgical forceps. Advantageously, the use of a material that makes it possible to convey light from the gripping zone 901 towards the distal body 902 makes it possible to improve the vision of the surgeon over the operating site. Moreover, a transverse bore 905 is made in the distal body 902 of the surgical instrument 900 and the two ends 906 of a thread made of an elastic material are introduced into bore 905 so as to form an elastic ring 907. Such an elastic ring is, for example, formed from polyamide, polyoxymethylene (POM) or from metal. The diameter of the elastic ring 907 is adapted to the diameter of a prosthesis 200 intended to be introduced into the hernial defect 100 in such a way that the diameter of the elastic ring 907 is at least greater than the diameter of the orifice 204 but smaller than the diameter of internal space 203. While the clamping means 903 clamp the first layer 201 of the prosthesis 200, the elastic ring 907 is introduced into the orifice 204 of prosthesis 200. Elastic deformation of the elastic ring 907 enables it to be introduced into the internal space 203 of the prosthesis 200 via the orifice 204. At rest, the elastic ring 907, introduced into the internal space 203, ensures complete deployment of prosthesis 200. When the elastic ring 907 is positioned as described previously in the internal space 203 of the prosthesis 200, the assembly defined by the prosthesis 200 and the surgical instrument 900 may be introduced into the hernial defect 100. The flexibility of the elastic ring 907 allows the assembly to be deformed in order to penetrate into the incision made by the surgeon. Once the distal body 902 and the prosthesis 200 are in the abdominal cavity 109, the elastic ring 907 returns to its initial shape thus ensuring deployment of the prosthesis 200.

When the surgical fastener 600 from FIG. 6 is introduced into the prosthesis 200 from FIG. 2 or 4, placed in the abdominal cavity 109, the surgeon may optionally remove the at least one return thread 208 before bringing, with the aid of the attachment arm 604, the first layer 201 of the prosthesis 200 into contact with the abdominal wall 101. Once the assembly made up of the prosthesis 200 and of the surgical fastener 600 is correctly centred in the hernial defect 100, the surgeon ensures that no viscera 106 is interposed between the prosthesis 200 and the abdominal wall 101, then anchors the attachment arm 604 of the surgical fastener 600 into the abdominal wall 101 (cf. FIG. 10).

Alternatively, when the attachment arm is completely introduced into the internal space 203 of the prosthesis 200, the prosthesis is then attached, for example, via at least one suture thread passed around attachment arm 604 and around one part of the abdominal wall 101.

FIG. 10 shows a repair of a hernial defect 100 carried out using a prosthesis 200 from FIG. 2 or 4, attached to the abdominal wall 101 using a surgical fastener 600 from FIG. 6. It appears in FIG. 10 that the length of attachment arm 604 is advantageously chosen so as to ensure correct anchoring and centring. The open ring 601 of the surgical fastener 600, by extending along the substantially circular peripheral contour 206, makes it possible to maintain an optimized contact of the prosthesis 200 with the abdominal wall 101 while allowing rigidification and correct and fold-free deployment of the second layer 202 of prosthesis 200. Such an attachment of the prosthesis 200 using the surgical fastener 600 is carried out without staples, thus avoiding the tensions that are a source of recurrence and pain for the patient. The second layer 202 of the prosthesis 200 thus attached is substantially flat and free of folds. Such a substantially flat contact surface with the viscera 106 is less traumatic and makes it possible to minimize the risks of recurrence.

The connection between the attachment arm 604 and the open ring 601 enables the attachment arm to extend in at least several different planes in order to allow anchoring in the abdominal wall. In the embodiment shown in FIG. 6, the attachment arm 604 consists of a single piece with the reinforcing section and the connection may undergo torsional stresses. In this embodiment, the attachment arm 604 is advantageously anchored in the abdominal wall so that the connection is maintained under torsional stress in order to ensure that the open ring 601 bears against the abdominal wall 101 thus ensuring an optimal contact of the first layer 201 of the prosthesis 200 with the abdominal wall 101.

The present disclosure also relates to a method for treating or preventing a hernial defect in the umbilical region, using a prosthesis and at least one surgical fastener as described above. In the present method, an incision is made in the abdominal wall at the hernial defect. After treating the hernial defect, the prosthesis is introduced into the incision in the manner described above. A surgical fastener according to the present disclosure is introduced into the internal space of the prosthesis. Then, the open ring is positioned bearing against the abdominal wall and the attachment arm is anchored into the abdominal wall.

In embodiments, the prosthesis is introduced into the incision by means of an introduction system as described above.

In other embodiments, the prosthesis may be introduced and positioned using a surgical instrument contained in the kit according to the present disclosure and as described previously.

The surgical fastener may be introduced into the internal space of the prosthesis, by its free end or by its end connected to the attachment arm, via the introduction opening made in the prosthesis.

The invention claimed is:

1. A surgical kit for treating a hernial defect of the abdominal wall comprising:
a surgical fastener for attaching a prosthesis intended to repair a hernial defect of the abdominal wall, said prosthesis comprising at least a first layer made of a biocompatible flexible material intended to be placed facing the abdominal wall and at least a second layer made of a biocompatible flexible material intended to be placed facing the abdominal cavity, said first and second layers being joined together at least one assembly zone, so as to define an internal space delimited by a substantially circular peripheral contour, said internal space being accessible to said surgical fastener by means of an introduction opening made in at least one of said first or second layers said surgical fastener comprising at least one body that forms a reinforcing section comprising an open ring substantially included into one plane and intended to extend substantially along at least one part of said substantially circular peripheral contour, said open ring defining two opposite ends, said fastener being intended to be introduced via said introduction opening into said internal space via at least one of said ends one of the ends of said open ring being connected to an attachment arm that extends substantially radially towards the inside of said open ring and is intended to be anchored in the abdominal wall, wherein said prosthesis comprises at least one return thread attached in the vicinity of said introduction opening.

2. A surgical kit according to claim 1, wherein said open ring forms an angular sector of at least 270°.

3. A surgical kit according to claim 1, wherein said open ring forms an angular sector of at least 340°.

4. A surgical kit according to claim 1, wherein the connection between said attachment arm and said open ring enables said attachment arm to extend in several different planes.

5. A surgical kit according to claim 1, wherein said attachment arm is equipped with attachment means.

6. A surgical kit according to claim 5 wherein said attachment means comprises concentric outer grooves.

7. A surgical kit according to 5, wherein said attachment means comprises outer ribs.

8. A surgical kit according to claim 5 wherein said attachment means comprises a harpoon.

9. A surgical kit according to claim 1, wherein the attachment arm consists of a single piece with the reinforcing section.

10. A surgical kit according to claim 9, wherein the connection between said attachment arm and said open ring is a bend of the reinforcing section.

11. A surgical kit according to claim 1, wherein the surface of said surgical fastener is substantially smooth.

12. A surgical kit according to claim 1, made from a bioresorbable material.

13. A surgical kit according to claim 1, further comprising a surgical instrument for positioning said prosthesis, said surgical instrument comprising at least one proximal gripping zone and at least one distal body said distal body being equipped with clamping means capable of grasping the first layer in the vicinity of said introduction opening and of moving it away from said second layer.

14. A surgical kit according to claim 13, wherein a transverse bore is made in the distal body of said surgical instrument in order that the ends of an elastic thread can be introduced into said transverse bore, said elastic thread forming an elastic ring.

* * * * *